United States Patent [19]

Lew

[11] 4,345,026

[45] Aug. 17, 1982

[54] MUTAGENICITY ASSAY

[75] Inventor: Kenneth K. Lew, Brookline, Mass.

[73] Assignee: The Children's Hospital Medical Center, Boston, Mass.

[21] Appl. No.: 224,100

[22] Filed: Jan. 12, 1981

[51] Int. Cl.³ .............................................. C12Q 1/00
[52] U.S. Cl. ........................................ 435/4; 435/29; 435/172; 435/6
[58] Field of Search ...................... 435/4, 6, 5, 29, 172

[56] References Cited

U.S. PATENT DOCUMENTS

| | | | |
|---|---|---|---|
| 3,816,263 | 6/1974 | Rabin et al. ...................... | 195/103.5 |
| 4,066,510 | 1/1978 | Thilly .............................. | 195/103.5 |
| 4,072,574 | 2/1978 | Loeb et al. ....................... | 195/103.5 |

OTHER PUBLICATIONS

Ames et al., "Carcinogens are Mutagens: A Simple System Combining Liver Homogenates for Activation and Bacteria for Detection", *Proc. Nat. Acad. Sci. USA.*, vol. 7, No. 8, (Aug. 1973), pp. 2281-2285.

Ames et al., "Methods for Detecting Carcinogens and Mutagens with the Salmonella/Mammalian-Microsome Mutagencity Test", *Mutation Research*, 31, (1975), pp. 347-364.

Cedric I. Davern, Genetics, Readings from Scientific American, pp. 2-17, 1979.

*Primary Examiner*—Robert J. Warden

[57] ABSTRACT

Mutagenicity assay method involving exposing a population of an animal species to a suspected mutagen and then scoring the occurrence, in a subsequent generation, of animals of a size substantially different from that of the exposed population as a measure of the mutagenicity of the suspected mutagen.

14 Claims, No Drawings

MUTAGENICITY ASSAY

The invention described herein was made in the course of work under a grant or award from the Department of Health and Human Services.

BACKGROUND OF THE INVENTION

This invention relates to mutagenicity assay methods.

Several laboratory tests currently in use measure mutagenicity. The object of most such tests is to determine, indirectly, whether a substance is a human carcinogen; the underlying theory is that a mutagen is likely also to be a carcinogen.

Some tests employ in vitro methods (Rabin et al. U.S. Pat. No. 3,816,263; Loeb et al. U.S. Pat. No. 4,072,574) while others, such as the widely-used Ames test, are in vivo assays. The Ames test, described in Ames et al. (1975), Mutation Research 31, 347 and Ames et al. (1973), Proc. Natl. Acad. Sci. U.S.A. 70, 2281, involves exposing auxotrophic bacteria to a suspected carcinogen and scoring revertants to wild-type.

According to another in vivo mutagenicity assay, described in Thilly U.S. Pat. No. 4,066,510, cultured human lymphoblasts, rather than bacteria, are exposed to a suspected mutagen and then scored for mutations.

SUMMARY OF THE INVENTION

I have discovered a mutagenicity assay method which employs whole living animals. The method involves exposing a population of an animal species to a suspected mutagen and then scoring the occurrence, in a subsequent generation, of animals of a size substantially different from that of the exposed population as a measure of the mutagenicity of the suspected mutagen.

In preferred embodiments, the exposed population is a mutant population, the subsequent generation is the $F_2$ generation, and the animal species used is the hermaphroditic nematode *Caenorhabditic elegans*.

The new method allows the observation of the effects of suspected mutagens on entire animals, in particular on eukaryotes, believed to be biochemically more similar to humans than are bacteria. Further, the use of size as the scored trait renders the method susceptable of automation.

DESCRIPTION OF THE PREFERRED EMBODIMENTS

We turn now to the description of the preferred embodiments.

Mutant Selection

Young larvae of the hermaphroditic nematode species *Caenorhabditis elegans* were exposed to the mutagen ethyl methanesulfonate and allowed to self-fertilize and lay eggs. The resulting $F_1$ generation was allowed to reproduce, and the $F_2$ generation was then screened for mutants substantially smaller in size than members of the wild-type $F_0$ generation. Those mutants were individually cloned, and those breeding true were then backcrossed with wild-type males (which occur at a rate of about 1 in 700 in a wild-type population); those mutants not segregating in such a way as to indicate a single locus mutation were discarded. Of the mutant animals in which the mutation was determined to behave as a single locus mutation, those animals were selected which both had an extremely low rate of spontaneous reversion to normal size, and a fairly high rate of mutation to normal size when treated with a mutagen.

Mutagenesis Assay

A generation of synchronous small mutants was obtained by first growing mutants on a lawn of bacteria and then flushing exponentially growing animals with 0.1 M NaCl, washing off the animals but not the sticky eggs. The eggs and embryos (the $F_0$ generation) were incubated for 24 hours and newly hatched animals were then concentrated to 100,000 animals/ml.

To 100 μl of 0.1 M NaCl solution containing 10,000 animals were added 4 μl of a mutagen dissolved in dimethylsulfoxide (DMSO). The animals were incubated with the test chemical dissolved in DMSO for 24 hours at 20° C. The survivors were then plated onto NGM plates seeded with a lawn of *E. Coli*; the animals were allowed to mature and to lay 50–100 eggs each. After allowing the embryos to hatch (the $F_1$ generation) and mature, the exponentially growing $F_1$ animals were allowed to lay eggs, and the next generation ($F_2$) was synchronized as previously described.

The $F_2$ animals were allowed to grow to adults, which were scored for mutational events producing large wild-type animals. Scoring was performed using filters to separate large and small animals. Animals were suspended in 0.1 M NaCl and given 17 minutes to swim through a Nitex uniform nylon mesh filter having 53μ pores. The animals not passing through were then allowed to swim for 13 minutes through a 60μ mesh filter. Finally, the animals failing to pass through the 60μ filter were collected with a 30μ mesh filter by vacumm and the trapped animals were allowed to recover at 20° C. for eighteen hours on NGM agar plates. The large-sized animals on the plate were then counted, their number being a measure of the mutagenicity of the test chemical. Large-sized animals were also routinely cloned to assure that they bred true for large size.

Chemical Resistance Assay

According to a second preferred embodiment, the animals exposed to the suspected mutagen are wild-type animals, and scored animals in the $F_2$ generation are mutants rather than revertants to wild-type.

A generation of synchronous wild-type *C. elegans* was obtained as described above for small mutants, and then exposed to the test chemical in DMSO and allowed to reproduce as described above. The $F_2$ adults were then exposed to the phorbol ester, phorbol -12-myristate 13 acetate, which causes wild-type animals to greatly shrink in size. Scoring was performed using filters, as described above, with large animals representing mutational events conferring resistance to the chemical.

Other Embodiments

Other embodiments are within the following claims. For example, any animal species in which mutation can cause a substantial increase or decrease in size can be used. When reversion to wild-type is being scored, the size relationship between wild-type and mutant can be reversed, i.e., the mutants on which suspected mutagens are tested can be abnormally large, rather than small, and reversions to small size scored.

When hermaphroditic nematodes are used, generations can be synchronized by using a chemical such as NaOCl, which kills animals but not embryos. It is not necessary, however, to use a hermaphroditic animal species. Below is a scheme for practicing the invention using any heterogametic animal species.

A population of female animals in which a size trait is carried on the X chromosome are exposed to a mutagen so that, in a portion of the animals, an X chromosome incurs a recessive mutation at a size-determining locus; these chromosomes are represented as $X^-$. The females are then crossed with wild-type males, producing offspring having the genotypes: $X^+X^+$, $X^-X^+$, $X^-Y$, and $X^+Y$. Of the four genotypes, only the $X^-Y$ males are phenotypically different in size from wild-type.

The mutant males are then randomly crossed with their sisters, producing some $X^-X^-$ females and $X^-Y$ males. These are crossed, giving rise to a pure population of mutant-sized animals.

The homozygous mutant ($X^-X^-$) females are then synchronized and exposed to the suspected mutagen, giving rise to some $X^+Y$ males. The wild-type males resulting from this cross are scored as representing mutational events; these males carry the revertant $X^+$ from the mutated female parent.

I claim:

1. A mutagenicity assay method comprising
   exposing a population of a eukaryotic animal species to a suspected mutagen, said animal species being a species in which mutation can cause an increase or decrease in size and in which said mutation behaves as a single locus mutation, and
   scoring the occurrence, in a subsequent generation, of animals of a size different from that of said exposed population as a measure of the mutagenicity of said suspected mutagen.

2. The method of claim 1 wherein said exposed population comprises a population mutant with respect to wild-type animals.

3. The method of claim 1 wherein said subsequent generation is the $F_2$ generation.

4. The method of claim 3, further comprising, prior to said scoring, synchronizing members of said $F_2$ generation.

5. The method of claim 4 wherein said synchronizing comprises separating animals from eggs and embryos comprising said $F_2$ generation.

6. The method of claim 5 wherein said separating comprises flushing the parent generation of said $F_2$ generation, after said parent generation has been allowed to lay eggs comprising said $F_2$ generation, with a solution capable of washing away said parent generation but not said eggs and embyos comprising said $F_2$ generation.

7. The method of claim 6 wherein said solution comprises dilute NaCl.

8. The method of claim 5 wherein said separating comprises exposing the parent generation of said $F_2$ generation, after said parent generation has been allowed to lay egges comprising said $F_2$ generation, to an agent capable of killing substantially all of said parent generation while leaving unharmed substantially all of said eggs and embryos comprising said $F_2$ generation.

9. The method of claim 8 wherein said agent comprises NaOCl.

10. The method of claim 1 wherein said animal species is a hermaphroditic species.

11. The method of claim 10 wherein said hermaphroditic species is a hermaphroditic nematode species.

12. The method of claim 11 wherein said nematode species is *Caenorhabditis elegans*.

13. The method of claim 1 wherein
    said animal species is a heterogametic species, and
    said exposed population are females each carrying on both X chromosomes a recessive gene for said substantially different size.

14. The method of claim 13 wherein said animals of a size different from that of said exposed population are revertant wild-type males.

* * * * *